United States Patent [19]

Itoh et al.

[11] Patent Number: 4,979,518
[45] Date of Patent: Dec. 25, 1990

[54] BODY DEPTH HEATING HYPERTHERMAL APPARATUS

[75] Inventors: Hideki Itoh, Kokubunji; Tsutomu Okada, Hachioji; Fumiaki Ishii, Hachioji; Minoru Shinotsuka, Hachioji; Yoshihito Shimizu, Hachioji, all of Japan

[73] Assignee: Olympus Optical Co., Ltd., Tokyo, Japan

[21] Appl. No.: 249,477

[22] Filed: Sep. 23, 1988

Related U.S. Application Data

[62] Division of Ser. No. 61,250, Jun. 12, 1987, abandoned.

[30] Foreign Application Priority Data

Jun. 13, 1986 [JP] Japan .................................. 61-137713
Jun. 20, 1986 [JP] Japan .................................. 61-145660

[51] Int. Cl.⁵ .............................................. A61N 1/06
[52] U.S. Cl. ..................................... 128/785; 128/804; 128/401; 606/28
[58] Field of Search ........................ 128/804, 784–786, 128/401, 303.1; 600/10; 606/27, 28

[56] References Cited

U.S. PATENT DOCUMENTS

| 1,807,105 | 5/1931 | Schliephake .................. 128/804 |
| 4,016,886 | 4/1977 | Doss et al. .................. 128/804 X |
| 4,323,056 | 4/1982 | Borrelli et al. .................. 128/804 X |
| 4,587,978 | 5/1986 | Suyama et al. .................. 128/804 |
| 4,674,481 | 6/1987 | Boddie, Jr. et al. ............ 128/804 X |

FOREIGN PATENT DOCUMENTS

| 7920927 | 2/1981 | France . |
| 206078 | 1/1984 | German Democratic Rep. . |
| 59-135067 | 3/1984 | Japan . |
| 59-69716 | 5/1984 | Japan . |
| 60-180442 | 11/1985 | Japan . |

*Primary Examiner*—Lee S. Cohen
*Attorney, Agent, or Firm*—Armstrong, Nikaido, Marmelstein, Kubovcik & Murray

[57] ABSTRACT

A hyperthermal apparatus comprises a hollow tube insertable into a body cavity. The tube has a body liquid draining path, and is formed of a heat generating substance or a substance generating heat by absorbing an electromagnetic energy fed from outside the body. The tube is detainable in a position likely to be closed.

17 Claims, 10 Drawing Sheets

BODY DEPTH HEATING HYPERTHERMAL APPARATUS

This is a division, of application Serial No. 061,250 filed June 12, 1987, now abandoned.

FIELD OF THE INVENTION AND RELATED ART

This invention relates to a body depth heating hyperthermal apparatus provided with a hollow heater for hyperthermally heating an affected part.

BACKGROUND OF THE INVENTION

Recently, a high frequency hyperthermal method has been developed where a cancerous tumor is destroyed by heating the affected part utilizing the fact that cancer cells are weaker against heat than normal cells.

In a high frequency hyperthermal method disclosed in a prior art example, such as Japanese Patent Laid Open No. 135067/1984, a conductive material such as a metal needle is arranged in the position of an object to be heated (cured) as an affected part in a living body. The position to be heated is held with a pair of opposed electrodes and a high frequency current is mad®to flow between both electrodes to concentrate the electric field at the metal needle and locally heat the part near the metal needle The above mentioned prior art example requires surgical treatment to set and remove the metal needle, thereby increasing the burden on the patient and has not often been practical in case the patient is in a weakened state.

One defect with the above mentioned hyperthermal method, is when it is used in a biliary duct closure. The internal pressure within the biliary duct will rise before the therapeutic effect is obtained and, unless the liquid is drained, death can occur Japanese Utility Model Laid Open No. 69716/1984 discloses a hollow tubular heater for curing cancers. One defect with this prior art example is that it requires lead wires ;or heating. Therefore, the heater gives the patient an unpleasant feeling and, during meal time, the lead wires will be in the way.

On the other hand, When a narrowed part is made in the end part of a biliary duct, a hollow tubular detainable tube is detained to prevent the biliary duct from being closed as disclosed, for example, in Japanese Utility Model Laid Open No. 180442/1985.

Figure 1:
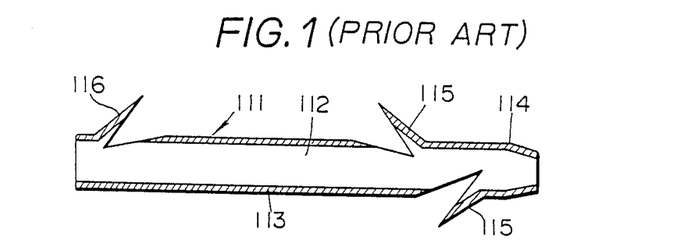
FIG. 1 is a sectioned view showing a prior art example.

As shown in FIG. 1, in the detainable tube 111, a tube body 113, having an inner cavity 112, is tapered on one end to form an opened tip part 114. The tube body 113 is provided with escape preventing flaps 115 near the tip part 114 and 116 on the other end.

However, when the cause of making a narrowed part in a biliary duct is due to a cancerous tumor, the above mentioned conventional detainable tube 111 will not be able to fundamentally cure the closure.

Also, USP 4,587,978 discloses a means of heating a body depth from outside the body but does not disclose a means to be detained within the body or a method of coping with the disease that closes the biliary duct.

OBJECTS AND SUMMARY OF THE INVENTION

An object of the present invention is to provide a body depth heating hyperthermal apparatus which can be detained in a closing position within a body to heat and to cure it.

Another object of the present invention is to provide a body depth heating hyperthermal apparatus which can be detained Within a body by means of an endoscope or the like without requiring a treatment.

A further object of the present invention is to provide a body depth heating hyperthermal apparatus which, even when detained within the body, will be able to allow the patient to continue normal activities as a healthy person.

In the present invention, the body depth heating hyperthermal apparatus can be inserted into a body cavity using an endoscope or the like. The apparatus has a body liquid draining path and is formed of a heat generating substance or an electromagnetic energy absorbing substance absorbing electromagnetic energy from an outside energy feeding source so as to be able to be detained in a position which is likely to be closed. The apparatus is able to hyperthermally cure an affected part by heating.

BRIEF DESCRIPTION OF THE DRAWINGS

FIGS. 2 and 3 relate to the first embodiment of the present invention;

FIGS. 13 and 14 relate to the eighth embodiment the present invention;

DETAILED DESCRIPTION OF PREFERRED EMBODIMENTS

Figures 2, 3:
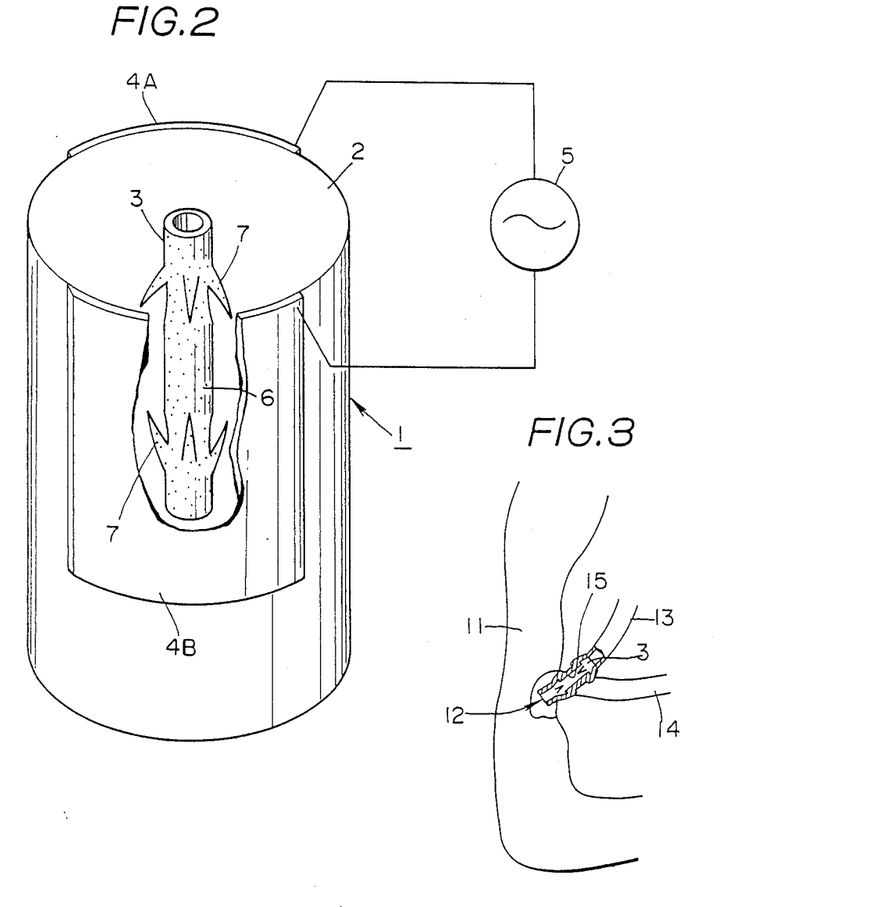
FIG. 2 is a schematic formation view of the first embodiment.
FIG. 3 is an explanatory view showing an example of using the first embodiment.

As shown in FIG. 2, a body depth heating hyperthermal apparatus 1 of the first embodiment is formed of a substantially cylindrical tubular heater 3 to be detained in a position to be hyperthermally cured within a living body. A pair of electrodes 4A and 4B output high frequency waves and are opposed to each other on the outer surface of the living body Within which the heater 3 is detained. A high frequency current source 5 has a high frequency current flowing between both electrodes 4A and 4B through lead wires connected to the electrodes 4A and 4B.

The above mentioned heater 3 is formed to be flexible and tubular of vinyl chloride, polyurethane, nylon, tetrafluoropropylene or polyethylene. The heater 3 has a metal powder 6 kneaded into it so as to have a conductivity higher than that of the tissue of the living body 2 and to increase the loss of high frequency waves in order to generate heat.

The tubular heater 3 has flaps 7 formed near both ends so as not to simply drop out of a narrowed part of the body when it is detained in the narrowed part.

The first embodiment can be used even in a narrowed part. For example, the manner of hyperthermally curing a narrowed part of a biliary duct shall be explained with reference to FIG. 3.

A duodenum nipple 12 opens on the way to a duodenum downward leg 11 and a biliary duct 13 and pancreatic duct 14 are connected to the duodenum nipple 12. It is assumed that a narrowed part 15 is produced by a cancerous tumor in the biliary duct.

A flexible sheath is inserted through a channel in an endoscope for the narrowed part 15. The sheath is set on the tip side to push and expand the narrowed part 15 of the biliary duct 13. In setting the sheath, for example, as in Japanese Patent Laid Open No. 227771/1985 filed by the present applicant, a member expanding in the form of basket-forceps is inserted through the sheath and can be set while pushing and expanding the above mentioned narrowed part 15. The above mentioned tubular heater 3 is externally fitted on the outer periphery on the proximal side of the sheath and is pushed at the rear end with a pusher tube so as to be set in the narrowed part 15. Then, if the inside sheath is pulled out, the sheath 3 will be able to be detained as shown in FIG. 3. The heater 3 is provided with escape preventing flaps 7 on the outer peripheral surface so as to be positively detained in the narrowed part 15.

When the heater 3 is set as shown in the above mentioned FIG. 3, the electrodes 4A and 4B will be brought into intimate contact with positions opposed to each other on the body surface enclosing the position of the heater 3 and the current source switch of the high frequency current source 5 will be switched on to have a current flowing between both electrodes 4A and 4B. When the high frequency current is flowing, the metal powder 6 of the conductive material will be concentrated in the electric field. The loss in this concentrated part will be converted to a larger amount of heat than in the living body tissue and the entire heater 3 will generate heat so as to be able to heat the vicinity of the narrowed part 15. Thus, the part affected by the cancerous tumor can be heated to be hyperthermally cured.

The heating temperature can be easily controlled by adjusting the output of the high frequency current flowing to the living body 2. Since the above mentioned heater 3 is in the form of a detainable tube, the affected part of a patient, whose biliary duct is closed by the cancerous tumor, can be cured by the hyperthermal curing method. That is to say since the heater 3 is provided with a hollow path and is in the form of the above mentioned detainable tube, even in the life threatening conventional case caused by a rise in pressure within the biliary duct due to heat, liquid or gas will be able to be drained through the above mentioned hollow path and therefore the above mentioned pressure within the biliary duct will be able to be prevented from rising. That is to say, the hyperthermal curing method can be carried out while performing a life extending function.

As the above mentioned heater 3 can be orally inserted or the like, an affected part can be cured without surgery and the pain of the patient can be reduced. Even an older person whose physical strength has been reduced so much as to not be able to endure the treatment can be cured With the first embodiment without requiring surgery. Further, the above mentioned tubular heater 3 is to be embedded into a body so as to be able to physiologically drain the biliary juice or the like and is not partly exposed off of the body and, therefore, the patient can live the same life as a healthy person and can return to society.

Since the above mentioned heater 3 is provided with flaps 7, When it is s®t in the narrowed part 15 of the biliary duct 13, it will be able to be positively prevented from escaping. Therefore, the heater 3 can be detained in the most suitable position. Also, since the tubular heater 3 is flexible, even if it is detained in the biliary duct 13, it Will not greatly change the operation of the biliary duct and will be safe anatomically.

Figure 4:
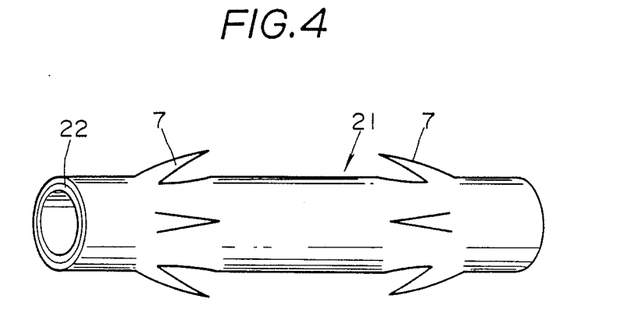
FIG. 4 is a perspective view showing a heater used in the second embodiment of the present invention.

FIG. 4 shows a heater 21 in the second embodiment of the present invention.

The heater 21 is formed to be a substantially cylindrical tube provided with flaps 7 of such high molecular weight resin as the above mentioned vinyl chloride. A metal pipe (or metal coil) 22 is fitted to the inner peripheral surface of the hollow path of the heater 21.

The heater 21 has substantially the same function and effect as the above mentioned first embodiment.

Figure 5:
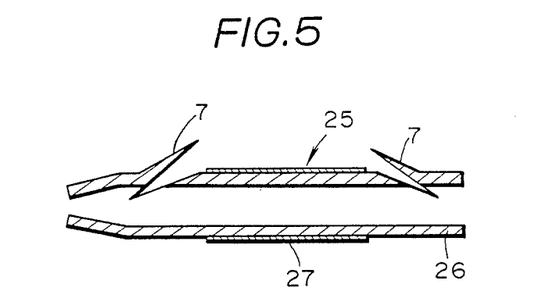
FIG. 5 is a sectioned view showing a modification of the heater in FIG. 3.

The metal-coated heater 25 as is shown in FIG. 5, may replace the above mentioned metal pipe 22. The heater 25 is provided With a metal coating 27 on the middle outer periphery of a flexible draining tube 26.

Figure 6:
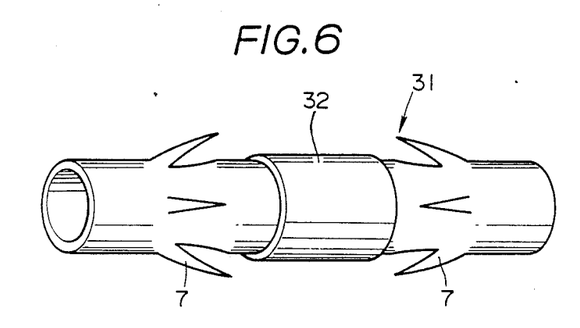
FIG. 6 is a sectioned view showing a heater relating to the third embodiment of the present invention.

FIG. 6 shows a heater 31 to be used in the third embodiment of the present invention.

Figure 7:
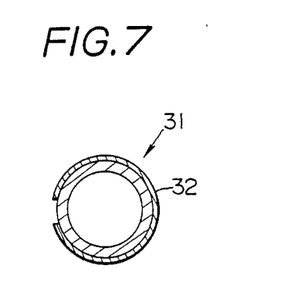
FIG. 7 is a sectioned view of FIG. 6.

The heater 31 is externally fitted with a metal ring 32 instead of using the metal pipe 22 in the above mentioned heater 21 in FIG. 3. As shown in FIG. 7, the metal pipe 32 is C-ring-shaped so as to be easy to fit to the outer periphery.

The above mentioned heater itself may be formed of a metal pipe.

Figure 8:
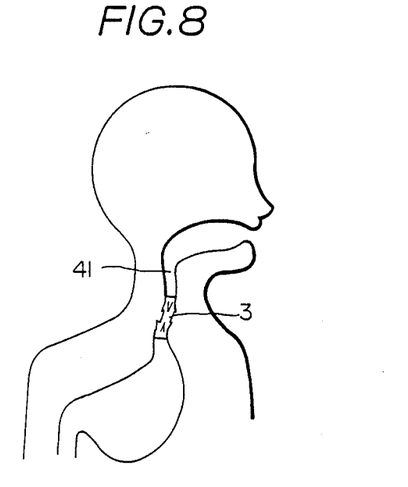
FIG. 8 is an explanatory view showing another example of using the present invention.

The above described example of using the device has been explained for the biliary duct but the present invention can be applied also to such other internal organ parts as a urethra. For example, the heater 3 can be used also in an esophagus 41 as shown in FIG. 8. In case it is used in the esophagus 41, the heater 3 will play a role of draining the food into the lower digesting tube instead of draining the biliary juice in the biliary duct.

The heater is not only made of the metal powder 6 or metal pipe 22 but is also made of a larger high frequency loss material which will pass higher frequency waves than in the living body tissue.

Figure 9:
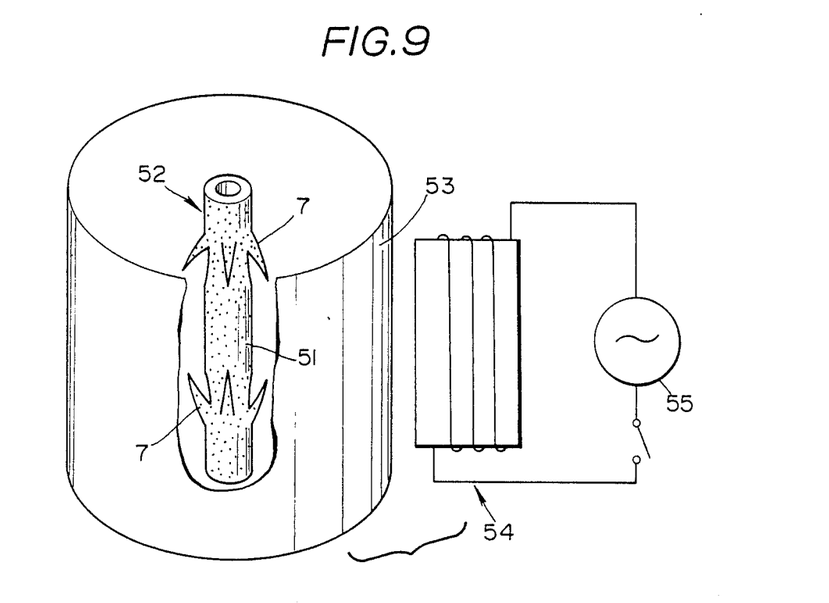
FIG. 9 is a schematic formation view of the fourth embodiment of the present invention.

FIG. 9 shows the schematic formation of the fourth embodiment of the present invention.

This fourth embodiment comprises a heater 52 formed by mixing a highly magnetic powder 51 in a flexible tube such as vinyl chloride. A magnetic field generator 54 is disposed near the body surface 53 around the heater 52 and a current source 55 feeds an electric power to the magnetic field generator 54.

The above mentioned heater 52 is provided with the same flaps 7 as in the above mentioned respective embodiments.

In this fourth embodiment, an alternating current magnetic field is generated by a magnetic field generator 54 such as an electromagnet. The alternating current magnetic field is concentrated on the heater 52 in which the highly magnetic powder 51 is mixed. The highly magnetic powder 51 of the heater 52 has a large loss of the above mentioned alternating current magnetic field or has a large loss of the used frequency. Therefore, the frequency is converted to heat in the heater 52 and the entire heater 52 is heated.

This fourth embodiment is not always required to be in close contact with the body surface 53 and, therefore, the affected part can be heated without giving an unpleasant feeling to the patient's body surface. Therefore, the magnetic field generator can be located outside of the patient's clothing. An advantage of using the fourth embodiment is that since the magnetic field generator 54 may be set on the underside of the bed on which the patient lies or on the bed itself, the affected part can be hyperthermally cured without contacting the magnetic pole surface of the magnetic field generator 54 directly with the body surface of the patient. One example of using the pr(R)sent fourth embodiment, is when the embodiment is applied to a biliary duct or the like as in the above mentioned first embodiment.

Figure 10:
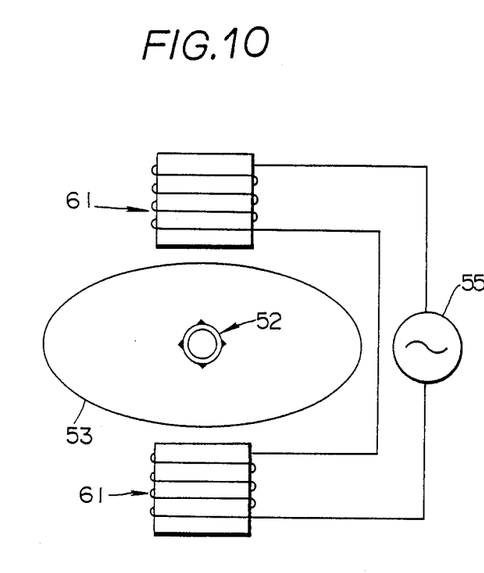
FIG. 10 is a schematic formation view of the fifth embodiment of the present invention.

FIG. 10 shows the fifth embodiment of the present invention.

In this fifth embodiment, a pair of magnetic field generators 61 are arranged as opposed to each other in positions in contact with or separated from the body surface 53 around the heater 52.

Figure 11:
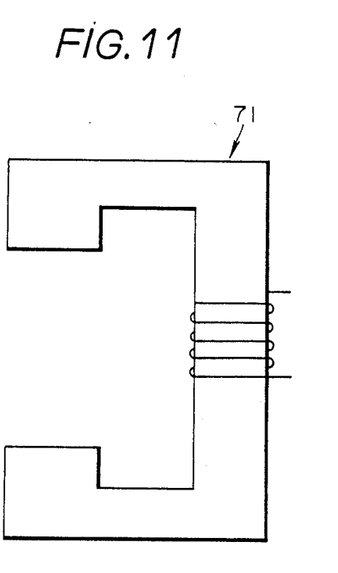
FIG. 11 is a plan view showing a magnetic field generator in the sixth embodiment of the present invention.

The above mentioned pair of the magnetic field generators 61 may be an integrated magnetic field generator 71 such as in the sixth embodiment of the present inVention shown in FIG. 11.

The heater may be made integral With an integral oscillator and temperature sensor and set in an object position so that the modulated degree or oscillated frequency of the oscillator may be varied with the sensed temperature of the temperature sensor. The oscillated output of the oscillator may be received by a receiver outside the body to monitor the hyperthermal temperature.

With the above mentioned received and sensed temperature, the output of the current source can be controlled so that the hyperthermal temperature may be automatically controlled to be constant. Also, the variation of the hyperthermal temperature with the lapse of time can be controlled to conform to a desired process.

If the above mentioned automatic control is made, even the variation of the generated heat amount in the heater, such as When the patient moves, Will be accommodated. Also, by accumulating the therapeutic data, the hyperthermia can be carried out by the process.

Figure 12:
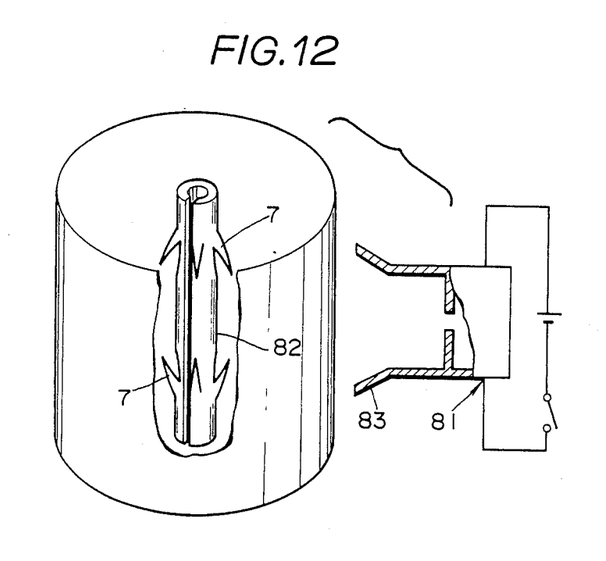
FIG. 12 is a formation view showing the seventh embodiment of the present invention.

In the seventh embodiment of the present invention shown in FIG. 12, electromagnetic waves such as microwaves can be radiated out of an electromagnetic wave generator 81 toward a heater 82 within the body without requiring the paired electrodes. In such a case, a substance which has a larger loss of microwaves or the like than is lost by living body tissues may be used for the heater 82.

The heater 82 is not limited to be tubular but may be C-ring-shaped as illustrated. When such a C-ring-shaped heater is used, it can be easily discharged out of the body by extracting it using a winding operation. Electromagnetic waves, such as microwaves, can be easily generated using a gun diode or the like with a battery or the like and the generated electromagnetic waves are emitted through an opening of a horn 83. The seventh embodiment can be portably used.

As described above, according to the first to seventh embodiments, since the heater (a) is provided with the hollow path through Which the body liquid or the like can pass; (b) can be set in the object position, and (c) is heated by passing a current from outside the body, even a position in which a closure such as a narrowed part is likely to be produced, can be hyperthermally cured without having the patient in pain.

An embodiment having a heating source in a tube body to be detained within a living body shall be explained by the following.

Figure 13:
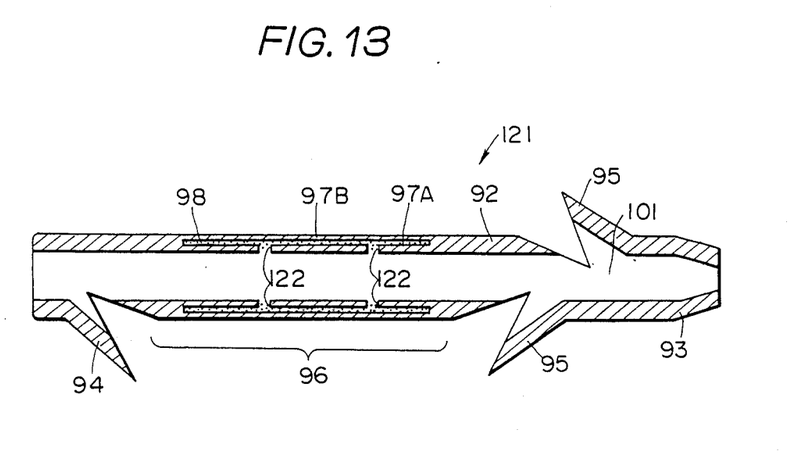
FIG. 13 is a sectioned view of the eighth embodiment.

As shown in FIG. 13, in a body depth heating hyperthermal apparatus 91 of the eighth embodiment, a hollow flexible tube 92 tubularly formed of a polyethylene material is tapered to be a small diameter on one end side to form a tip part 93 which is easy to insert. The tube 92 is provided with escape preventing flaps 94 and 95 to project respectively in the part adjacent to the tip part 93 and near the rear end part.

The middle part 96 of the above mentioned tube body 92 is formed of two layers having an inner layer tube part 97A and an outer layer tube part 97B. The cylindrical air gap part between these two inner and outer layer tube parts 97A and 97B is filled with a heat generating substance 98 generating heat by reacting with water as, for example, Ozomax (trade name of a substance developed by Ozo Chemical Technical Laboratory and mentioned, for example, in the *Daily Industrial Newspaper* of Oct. 15, 1985).

The heat generating substance 98 contained between the above mentioned inner layer and outer layer tube parts 97A and 97B generates heat by reacting with water coming in through small side holes 99 made on the outer layer tube part 97B.

In case the above mentioned detainable tube 91 is detained within a body, a liquid or gas will be able to be passed through an inner cavity 101 inside the tube.

The thus formed eighth embodiment is characterized by being formed to be tubular and being provided with the flaps 94 and 95 so as to be able to be detained in a tubular position within a body and with the heat generating substance 98 generating heat in a flameless state by reacting with water.

Therefore, in case a cancerous tumor which is weaker against heat than normal cells is produced, it will be able to be heated with this eighth embodiment as detained in the affected position in order to be treated.

Figure 14:
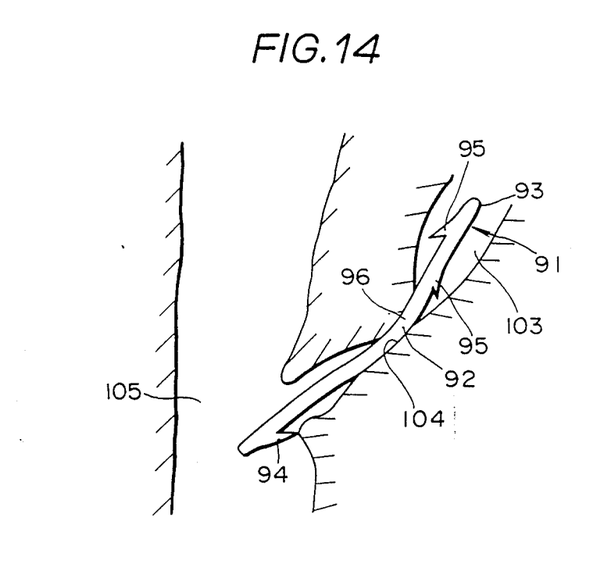
FIG. 14 is an explanatory view showing an example of using the eighth embodiment.

An example of using the above mentioned eighth embodiment shall be explained in the following with reference to FIG. 14.

For example, if a cancerous tumor is produced near the end of a biliary duct 103, a narrowed part 104 will be made. If this narrowd part is left untreated, it will become a closed part. The internal pressure of the biliary duct 103 will become so high that it can lead to death. In such a case, by using an endoscope, as shown in FIG. 14, the detainable tube 91 of the eighth embodiment is set to push and expand the narrowed part 104 with the middle part to make the biliary duct 103 and duodenum 105 communicate with each other through the inner cavity 101 of the detained tube 91 by inserting the endoscope on the tip side into the duodenum 105 through the inner cavity of the tube 91 and using a detainable tube guide means inserted through the channel in the endoscope. This setting method is disclosed, for example, in Japanese patent Laid Open No. 227771/1985.

The detainable tube 91 which is to push and to expand the above mentioned narrowed part 104, is provided with flaps 94 and 95. The tube 91 is, therefore, prevented from escaping out of the narrowed part 104 and is positively; detained. When the tube 91 is thus detained, the biliary juice on the upstream side of the biliary duct 103 will be drained onto the duodenum 105 through the inner cavity 101 and the biliary duct will be prevented from being closed.

The heat generating substance 98 contained in the above mentioned detainable tube 91 generates heat by reacting with the liquid entering the part containing the heat generating substance 98 through the side holes 99 on the tube body 92. Therefore, the tube body 92 is kept heated and heats the narrowed part 104 in contact with the middle part 96 of the tube body 92 so as to exterminate the cancer cells which are weakened by heat in order to cure the tumor.

Figure 15:
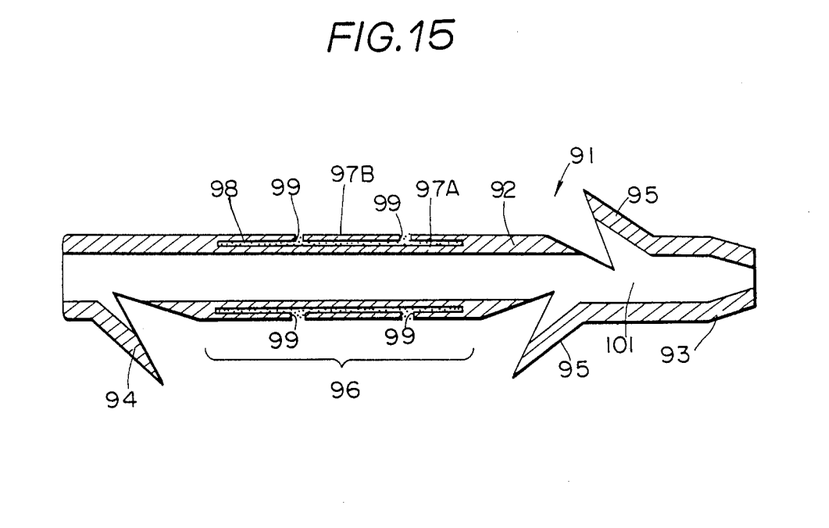
FIG. 15 is a sectioned view showing the ninth embodiment of the present invention.

FIG. 15 shows the ninth embodiment of the present invention.

The above mentioned eighth embodiment is provided with the side holes 99 on the outer layer tube part 97B side; whereas, the body depth heating hyperthermal apparatus 121 of the ninth embodiment is provided on the inner layer tube part 97A side with inner holes 122 communicating with the inner cavity 101.

Otherwise, the ninth embodiment is of the same formation as of the above mentioned eighth embodiment and the same parts are represented respectively by the same reference numerals.

In the ninth embodiment, in case the biliary juice passes through the inner cavity, it will enter the part containing the heat generating substance 98 through the inner holes 122 to react with the heat generating substance 98 to generate heat.

The ninth embodiment has substantially the same function and effect as of the aboVe mentioned eighth embodiment.

Figure 16:
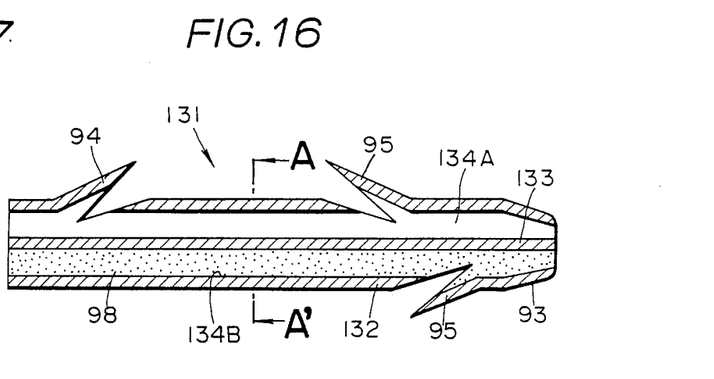
FIG. 16 is a sectioned view showing the tenth embodiment of the present invention.
Figure 17:
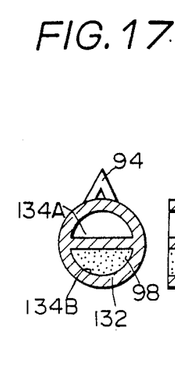
FIG. 17 is a sectioned view on line A—A' in FIG. 16.

FIG. 16 shows the tenth embodiment of the present invention.

In the detainable tube 131 of the tenth embodiment, the tube body 32 is not formed of two layers such as in the above mentioned eighth or ninth embodiment. The inner cavity is partitioned with a partitioning part 133 into a first inner cavity 134A and second inner cavity 134B. The second inner cavity 134B on one side is filled with a heat generating substance 98, such as Ozomax. The above mentioned first inner cavity 134A and the second inner cavity 134B filled with the heat generating substance 98 are opened at both ends. Therefore, liquid such as a biliary juice or a gas can pass through the first inner cavity 134A. When water, such as the biliary juice, enters the second inner caVity 134B from one of the open ends, the heat generating substance 98 Will react to generate heat without a flame. The second inner cavity 134B may be closed at both ends with net-like members so as to pass water but no heat generating substance 98. The function and effect of the tenth embodiment are substantially the same as the above mentioned eighth or ninth embodiment.

Figure 18:
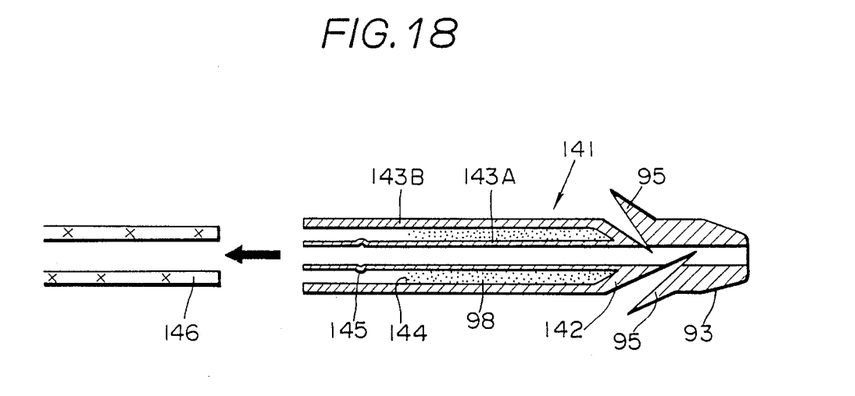
FIG. 18 is a sectioned view showing the eleventh embodiment of the present invention.

FIG. 18 shows the eleventh embodiment of the present invention.

In the body depth heating hyperthermal apparatus 141 of the eleventh embodiment, the tube body 142 is of a double structure having an inner layer tube part 143A and an outer layer tube part 143B extend from near the middle part of the tube body 142 to the end. The ring-shaped or cylindrical air gap part 144, formed of the outer peripheral surface of the inner layer tube part 143A and the inner peripheral surface of the outer layer tube part 143B, is filled with a heat generating substance 98, such as Ozomax.

A click 145, projecting to a outside direction is provided on the outer peripheral surface of tube part 143A near the end of the inner layer tube part 143A. A pushing tube 146, to be used to push the body depth heating hyperthermal apparatus 141 from the rear and detain it in the depth o; the body, can be fitted on the tip side into the air gap part 144 on the end side. The pushing tube 146 fitted in as shown in FIG. 19 from the state in FIG. 18 is held and pressed by the click 145 partly to prevent the entry of water.

Figure 19:
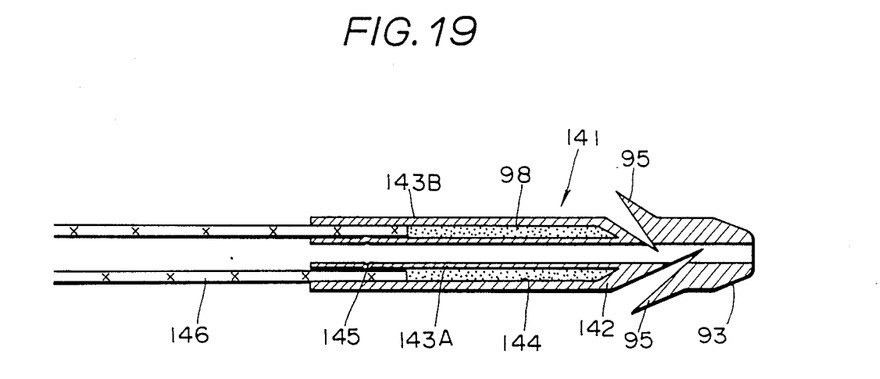
FIG. 19 is a sectioned view showing a pushing tube as fitted to the eleventh embodiment.

In the eleventh embodiment, the pushing tube 146 fitted into the air gap part 144 of the body depth heating hyperthermal apparatus 141 as shown in FIG. 19, pushes the body depth heating hyperthermal apparatus on the tip side into a narrowed part or closed part of a biliary duct and is then pulled out. Then, due to the removable of the pushing tube the air gap part 144 is opened on the end side. Therefore, the body liquid comes into the air gap part 144 and the heat generating substance 98 contained in the air gap part reacts to generate heat.

Figure 20:
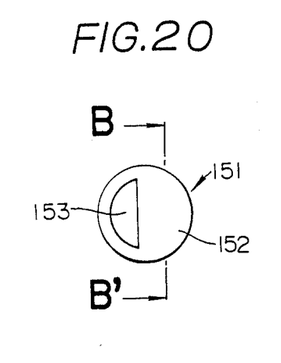
FIG. 20 is an elevation showing a tip of the twelfth embodiment of the present invention.
Figure 21:
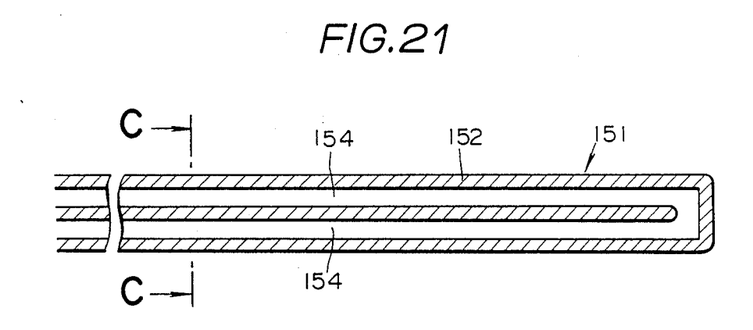
FIG. 21 is a sectioned view on line B—B' in FIG. 20.
Figure 22:
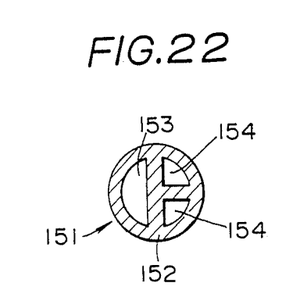
FIG. 22 is a sectioned view on line C-C' in FIG. 21.

FIGS. 20 to 22 show the twelfth embodiment of the present invention.

In this body depth heating hyperthermal apparatus, a tube body 152 is provided in half of the tube body with a draining hole 153 communicating from the tip to the end as shown in FIG. 20. The tube body 152 is also provided in the remaining half of the tube body with two reflux paths 154 connected with each other at the tip as shown in FIG. 22. The reflux paths 154 are closed at the tip as shown in FIG. 21.

Figure 23:
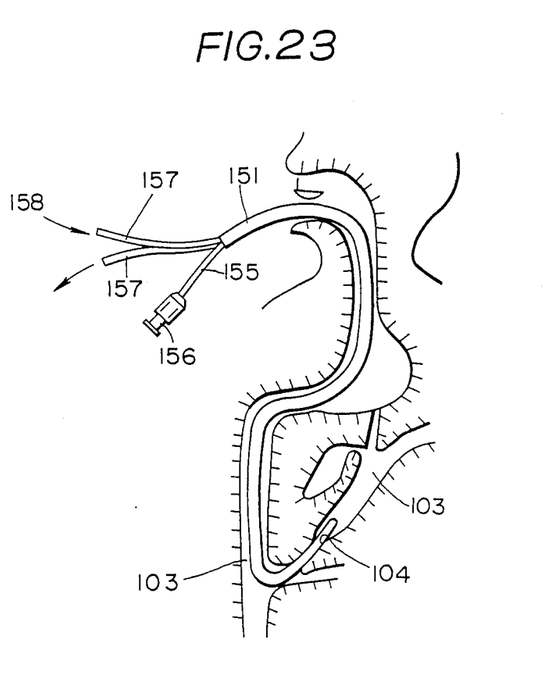
FIG. 23 is an explanatory view showing an example of using the twelfth embodiment.

The above mentioned body depth heating hyperthermal apparatus 151 is made long enough to be outside the mouth cavity on the proximal side when it pushes and expands on the tip side the narrowed part 104 of of the biliary duct 103 (through the endoscope) as shown, for example, in FIG. 23. At this proximal end, a connecting tube 155 is connected to the above mentioned draining hole 153 and a removable mouthpiece 156 can be fitted to the connecting tube 155. The biliary juice or the like can be drained out of the body through the connecting tube 155 are draining hole 153.

Connecting tubes 157 are connected respectively to the proximal ends of the reflux paths 154 in the body depth heating hyperthermal apparatus. Heat generating fluid 158 such as, for example, hot water is fed through one connecting tube 157 and can be recovered through the other connecting tube 157.

By circulating the above mentioned heat generating fluid 158 through the reflux paths 154 communicating with each other, the narrowed part of the biliary duct which has been pushed and expanded With the tip side part of the body depth heating hyperthermal apparatus 151 is heated and cured.

Figures 24, 25:
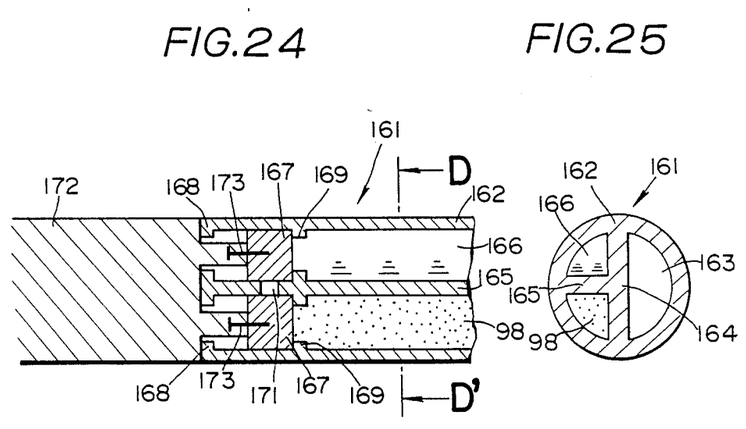
FIG. 24 is a sectioned view showing the thirteenth embodiment of the present invention.
FIG. 25 is a sectioned view on line D—D' in FIG. 24.

FIGS. 24 and 25 show the thirteenth embodiment of the present invention.

In this body depth heating hyperthermal apparatus 161, half of a tube body 162 of a proper length to be detained in a narrowed part within a body; is provided with a through hole 163 of a semicircular cross-section communicating at both ends. The air gap part of a semicircular cross-section partitioned with a partition film 164 from the through hole 163 side is further partitioned with a partition film 165 to form two containing parts the other half of the tube body 162. When a heat generating substance 98 such as Ozomax and water 166, are mixed to generate heat, the water and heat generating substance 98 are contained respectively in these containing parts. The containing parts are closed at the tips and also at the ends with movable valves 167 formed of elastic bodies or the like.

The respective movable valves 167 are made movable between projections 168 and 169 Which are proVided to project at the ends of the containing parts and in positions somewhat forward of the ends. When these movable valves 167 are moved from the positions shown in FIG. 24 to the rearWard positions in which they collide with the projections 168, both containing parts will be able to communicate with each other through an opening 171 provided near the end of the partition film 165. After the detainable tube body 162 is detained as follows by the pushing tube 172, it can be made to generate heat.

That is to say, needles 173 embedded at the front end of the pushing tube 172 are thrust on the tip sides into the movable valves 167 and the body depth heating hyperthermal apparatus 61 is pushed with the pushing tube 172 so as to be set in such a predetermined tubular position such as a narrowed part. When the pushing tube 172 is pulled on the proximal side so as to be pulled out of the body, both movable Valves 167 will move rearward (leftward) and both containing parts will communicate with each other through the opening 171. Therefore, the water 166 and heat generating substance 98 Will mix and react to generate heat.

Figure 26:
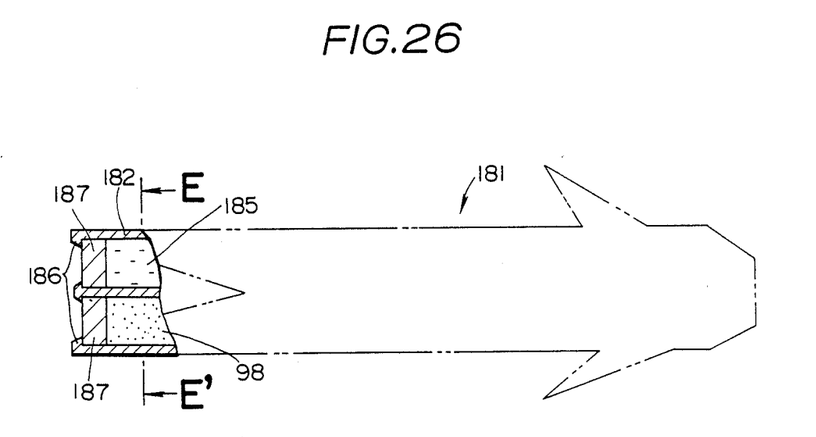
FIG. 26 is a sectioned view showing the fourteenth embodiment of the present invention.
Figure 27:
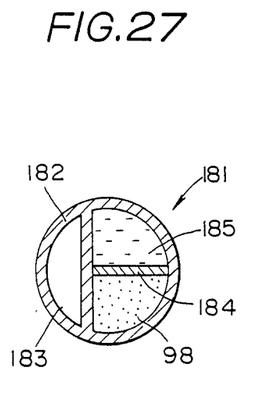
FIG. 27 is a sectioned view on line E—E' in FIG. 26.

FIGS. 26 and 27 shoW the fourteenth embodiment of the present invention.

In the body depth heating hyperthermal apparatus 181 of the fourteenth embodiment, as in the body depth heating hyperthermal apparatus 161 of the thirteenth embodiment shown in FIGS. 24 and 25, a tube body 182 is provided with a through hole 183 communicating at both ends and two containing parts closed at the tips are formed by being partitioned with a partition film 184. A heat generating substance 98 can be contained respectively in these containing parts through the opening ends and the containing parts can be closed respectively With rubber plugs 187, which are respectively prevented from being pulled out by projections 186.

In this fourteenth embodiment, the above mentioned partition film 184 is formed of a semi-transmissive film or the like which transmits water 185. Therefore, after the water 185 and heat generating substance 98 are contained respectively in both containing parts, a heat generating reaction will gradually occur by the water 185 passing through the semi-transmissive film. One advantage of this embodiment is that, by adjusting the thickness or only a part of the area of the partition film 184 made of the semi-transmissive film, the transmitted amount of water 185 can be adjusted and the heat generating temperature and time can be controlled. This body depth heating hyperthermal apparatus 181 is provided with flaps near the tip and near the end.

Figure 28:
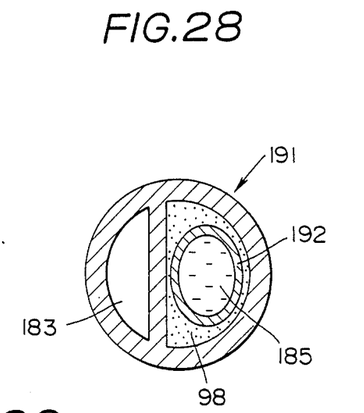
FIG. 28 is a sectioned view showing the fifteenth embodiment of the present invention.

FIG. 28 shows the fifteenth embodiment of the present invention.

In the body depth heating hyperthermal apparatus 191 of the fifteenth embodiment, the partition film 184 of the fourteenth embodiment is not provided. The containing part closed at the tip contains the heat generating substance 98 and a semi-transmissive bag 192. The containing part is closed at the opening end with a plug. The other parts of the fifteenth embodiment are substantially the same as in the above mentioned fourteenth embodiment. The fifteenth embodiment is of substantially the same function as the above mentioned fourteenth embodiment.

The semi-transmissive bag 192 may contain the heat generating substance 98 instead of water 185.

Figure 29:
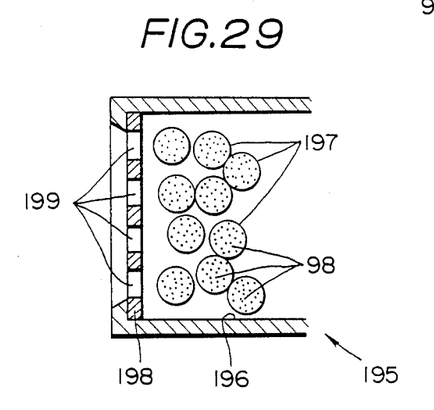
FIG. 29 is a sectioned view showing a part of the sixteenth embodiment.

FIG. 29 shows the sixteenth embodiment of the present invention.

The body depth heating hyperthermal apparatus 195 of the sixteenth embodiment is proVided with a first inner cavity and second inner cavity 196, for example, semicircular in cross-section the same as is shown in the above mentioned FIG. 16. The first inner cavity is a draining path through which biliary juice or the like can pass and the second inner cavity 196 is charged with semi-transmissive film balls containing the heat generating substance 98. The size of each semi-transmissive film ball 197 is made somewhat larger than of small holes 199 in a highly elastic lid 198 at the end of the second inner cavity 196. Small holes in a lid on the tip side are made smaller than on the end side.

When Water such as a biliary juice enters the above mentioned semi-transmissive film balls 197, heat will be generated. The reaction substance will not be able to pass through the semi-transmissive film and the ball diameter will become larger. Therefore, the balls enlarged in diameter within the second inner cavity 196 will pass the lid 198. The balls will push and expand the small holes 199, and will be pushed out of the body depth heating hyperthermal apparatus 195. Then, the balls will be drained out of the body.

In the sixteenth embodiment, the useless heat generating substance after the heat generating reaction can be drained out of the body. Also, in this case, for example, by mixing a substance such as a radioisotope into the semi-transmissive film balls 197 contain ®d on the tip side, from the drainage of the heat generating reaction substance, a determination can be made when the heat generating action has ended. Also, a substance which is easily distinguished from the drainage may be mixed therein.

In the present invention, the heat generating substance is not limited to Ozomax but may be a substance generating heat in contact with air or a substance mixed with special chemicals so as to generate heat by a chemical reaction or the like.

Also, the holes through which water comes in may be blocked with a substance soluble with the water or acid so that the amount of Water which can enter may be adjusted.

Generally, a heat generating reaction such as a hydrogenating reaction on an oxide, for example, in the case of calcium as represented by the formula:

$$CaO + H_2O \rightarrow Ca(OH)_2 + \text{heat generation}$$

may be utilized. A mixture of an iron powder and a metallic acid salt as a main component which causes an iron powder oxidizing reaction can be made into a heat generating unit. The mixture may be utilized to generate heat when the mixture contacts with Water and air Within a body or the like. A heat generating reaction caused by adding water to such an anhydride as acetic anhydride may also be utilized.

The heat generating substance may be covered with foaming material transmitting water vapor but no liquid such as, for example, tetrafluoroethylene to prevent the reaction product from having a bad influence on a human body. (As an example of this application, for example, in FIG. 28, the tube part enclosing the heat generating substance 98 may be made into a tube formed of a foaming material of tetrafluoroethylene). Also, the tube body may be a tube made of the above mentioned foaming material or a semi-transmissive tube.

The path through which a biliary juice or the like can pass is not limited to the inner cavity ©r hollow path of the tube but may be a groove-like path leading to both ends.

As described above, according to the eighth to sixteenth embodiments, a heating means for heating a tubular member having communicating paths communicating with each other at both ends is provided so that the biliary juice or the like may be drained and a tumor may be treated.

Although there have been described what are at present considered to be the preferred embodiments of the present invention, it will be understood that the invention may be embodied in other specific forms without departing from the spirit or essential characteristics thereof. The present embodiments are, therefore, to be considered in all aspects as illustrative, and not restrictive. The scope of the invention is indicated by the appended claims, rather than by the foregoing description.

What is claimed is:

1. A body depth heating hyperthermal apparatus comprising:
   a detainable tube insertable into a body cavity, said detainable tube having a body liquid draining path formed therethrough and being fitted with a metal member, said detainable tube being formed of an electromagnetic absorbent, said detainable tube provided with a supporting means for supporting said detainable tube in said body cavity;
   electrodes which are opposed to each other, said electrodes located outside the body cavity which holds said detainable tube; and
   an electromagnetic energy generating source, connected to said electrodes, feeding an electromagnetic energy to said electrodes.

2. A body depth heating hyperthermal apparatus according to claim 1, wherein said detainable tube is cylindrical.

3. A body depth heating hyperthermal apparatus according to any one of claims 1 or 2, wherein said detainable tube is flexible.

4. A body depth heating hyperthermal apparatus according to claims 1 or 2, wherein said supporting means has a plurality of flaps projecting outward.

5. A body depth heating hyperthermal apparatus according to claims 1 or 2, wherein said detainable tube is formed of a substance having a large high frequency loss.

6. A body depth heating hyperthermal apparatus according to claim 5, wherein said substance having a large high frequency loss is of a tube formed of a high molecular weight resin material.

7. A body depth heating hyperthermal apparatus according to claim 6, wherein said metal member is a metal ring fitted to said tube.

8. A body depth heating hyperthermal apparatus according to claim 6, wherein said metal member is a metal coating of said tube.

9. A body depth heating hyperthermal apparatus according to claim 1, wherein said supporting means is composed of flaps attached at each end of the detainable tube, said metal member formed between said flaps.

10. A body depth hyperthermal apparatus comprising:
    a detainable tube insertable into a body cavity, said detainable tube having a body liquid draining path formed therethrough and being fitted with a metal member, said detainable tube being formed of an electromagnetic absorbent and a substance having a large high frequency loss, said substance is a tube formed of a high molecular weight resin material, said detainable tube provided with a supporting means for supporting said detainable tube in said body cavity;
    electrodes which are opposed to each other, said electrodes located outside the body cavity which holds said detainable tube; and
    an electromagnetic energy generating source, connected to said electrodes, feeding an electromagnetic energy to said electrodes, feeding an electromagnetic energy to said electrodes, said electromagnetic energy generating source consisting of a high frequency generator.

11. A body depth heating hyperthermal apparatus comprising:
    a detainable tube insertable into a body cavity, said detainable tube having a body liquid draining path formed therethrough and being fitted with a metal member, said metal member is a metal ring fitted to said detainable tube, said detainable tube being formed of an electromagnetic absorbent and a substance having a large high frequency loss, said substance is a tube formed of a high molecular weight resin material, said detainable tube provided with a supporting means for supporting said detainable tube in said body cavity;
    electrodes which are opposed to each other, said electrodes located outside the body cavity which holds said detainable tube; and
    an electromagnetic energy generating source, connected to said electrodes, feeding an electromagnetic energy to said electrodes, said electromagnetic energy generating source consisting of a high frequency generator.

12. A body depth heating hyperthermal apparatus comprising:
   a detainable tube insertable into a body cavity, said detainable tube having a body liquid draining path formed therethrough and being fitted with a metal member, said metal member is a metal coating of said detainable tube, said detainable tube being formed of an electromagnetic absorbent and a substance having a large high frequency loss, said substance is a tube formed of a high molecular weight resin material, said detainable tube provided with a supporting means for supporting said detainable tube in said body cavity;
   electrodes which are opposed to each other, said electrodes located outside the body cavity which holds said detainable tube; and
   an electromagnetic energy generating source, connected to said electrodes, feeding an electromagnetic energy to said electrodes, said electromagnetic energy generating source consisting of a high frequency generator.

13. A body depth heating hyperthermal apparatus comprising:
   a detainable tube insertable into a body cavity, said detainable tube having a body liquid draining path formed therethrough and being fitted with a metal member, said detainable tube being formed of an electromagnetic absorbent and a substance having a large high frequency loss, said substance is of a tube formed of a high molecular weight resin material, said detainable tube being cylindrical, said detainable tube provided with a supporting means for supporting said detainable tube in said body cavity;
   electrodes which are opposed to each other, said electrodes located outside the body cavity which holds said detainable tube; and
   an electromagnetic energy generating source, connected to said electrodes, feeding an electromagnetic energy to said electrodes, said electromagnetic energy generating source consisting of a high frequency generator.

14. A body depth heating hyperthermal apparatus comprising:
   a detainable tube insertable into a body cavity, said detainable tube having a body liquid draining path formed therethrough and being fitted with a metal member, said metal member is a metal ring fitted to said detainable tube, said detainable tube being formed of an electromagnetic absorbent and a substance having a large high frequency loss, said substance is of a tube formed of a high molecular weight resin material, said detainable tube being cylindrical, said detainable tube provided with a supporting means for supporting said detainable tube in said body cavity;
   electrodes which are opposed to each other, said electrodes located outside the body cavity which holds said detainable tube; and
   an electromagnetic energy generating source, connected to said electrodes, feeding an electromagnetic energy to said electrodes, said electromagnetic energy generating source consisting of a high frequency generator.

15. A body depth heating hyperthermal apparatus comprising:
   a detainable tube insertable into a body cavity, said detainable tube having a body liquid draining path formed therethrough and being fitted with a metal member, said metal member is a metal coating of said detainable tube, said detainable tube being formed of an electromagnetic absorbent and a substance having a large high frequency loss, said substance is of a tube formed of a high molecular weight resin material, said detainable tube being cylindrical, said detainable tube provided with a supporting means for supporting said detainable tube in said body cavity;
   electrodes which are opposed to each other, said electrodes located outside the body cavity which holds said detainable tube; and
   an electromagnetic energy generating source, connected to said electrodes, feeding an electromagnetic energy to said electrodes, said electromagnetic energy generating source consisting of a high frequency generator.

16. A body depth heating hyperthermal apparatus comprising:
   a detainable tube insertable into a body cavity, said detainable tube having a body liquid draining path formed therethrough and being fitted with a metal member, said detainable tube being formed of an electromagnetic absorbent and a substance having a large high frequency loss, said detainable tube provided with a supporting means for supporting said detainable tube in said body cavity, said supporting means is composed of flaps attached at each end of the detainable tube, said metal member formed between said flaps;
   electrodes which are opposed to each other, said electrodes located outside the body cavity which holds said detainable tube; and
   an electromagnetic energy generating source, connected to said electrodes, feeding an electromagnetic energy to said electrodes.

17. A body depth heating hyperthermal apparatus comprising:
   a detainable tube insertable into a body cavity, said detainable tube having a body liquid draining path formed therethrough and being fitted with a metal member, said detainable tube being formed of an electromagnetic absorbent and a substance having a large high frequency loss, said detainable tube being cylindrical, said detainable tube provided with a supporting means for supporting said detainable tube in said body cavity, said supporting means is composed of flaps attached at each end of the detainable tube, said metal member formed between said flaps;
   electrodes which are opposed to each other, said electrodes located outside the body cavity which holds said detainable tube; and
   an electromagnetic energy generating source, connected to said electrodes, feeding an electromagnetic energy to said electrodes.

* * * * *

UNITED STATES PATENT AND TRADEMARK OFFICE
CERTIFICATE OF CORRECTION

PATENT NO. : 4,979,518

DATED : December 25, 1990

INVENTOR(S) : Hideo ITOH et al

It is certified that error appears in the above-identified patent and that said Letters Patent is hereby corrected as shown below:

On the cover page, Item [75], "Hideki Itoh" should read -- Hideo Itoh --.

Signed and Sealed this

Thirteenth Day of October, 1992

Attest:

DOUGLAS B. COMER

Attesting Officer

Acting Commissioner of Patents and Trademarks